United States Patent [19]

Lee et al.

[11] 4,279,259

[45] Jul. 21, 1981

[54] MAMMOMETER

[75] Inventors: Denis C. Lee, Ann Arbor; Arthur H. Rathjen, Midland, both of Mich.

[73] Assignee: Dow Corning Corporation, Midland, Mich.

[21] Appl. No.: 819,735

[22] Filed: Jul. 28, 1977

Related U.S. Application Data

[63] Continuation-in-part of Ser. No. 702,657, Jul. 6, 1976, abandoned.

[51] Int. Cl.³ .............................................. A61B 5/10
[52] U.S. Cl. ................................ 128/774; 33/174 B; 33/174 D
[58] Field of Search .................... 128/2 S, 303 R, 774; 3/36; 33/174 D, 174 B, 1 B, 2 R

[56] References Cited

U.S. PATENT DOCUMENTS

D. 141,882   7/1945   Matson ........................ 33/174 B X
2,559,501    7/1951   Graf ............................. 33/174 D Primary Examiner—Robert W. Michell
Assistant Examiner—Michael H. Thaler
Attorney, Agent, or Firm—Jack E. Moermond

[57] ABSTRACT

An article of manufacture is disclosed which is useful for making measurements of and relative to mammary glands. This article is of particular use to surgeons in various kinds of breast surgery. For example, this article can be used to assist in the selection of the appropriate size mammary prosthesis and the location of incision site.

5 Claims, 2 Drawing Figures

MAMMOMETER

This application is a continuation-in-part of application Ser. No. 702,657 filed July 6, 1976, now abandoned.

Heretofore in the various kinds of breast surgeries, ranging from reconstruction, to augmentation, correction of asymetry, reduction mammoplasty and mastopexy, the surgeon has primarily relied on his visual skills in making measuremental decisions with regard to the surgery to be performed.

It is an object of this invention to provide an article which is useful for making measurements of and relative to the mammary gland or breast.

Another object is to provide an article which is useful in the selection of the appropriate sized mammary prosthetic devices.

Still another object is to provide an article which is useful to surgeons in the location and placement of guideline marks for breast surgery.

Yet another object is to provide an article which will be useful to surgeons in various surgical procedures to provide patients with virtually identical and symmetrically located breasts.

Yet another object is to provide an article which a fitter of external prostheses and foundation garments would find useful when fitting women who have undergone unilaterial or bilateral mastectomies.

These and other objects and advantages of the article of the present invention will be apparent to those skilled in the art from the following detailed description, drawings and claims. In the drawings the same number is used throughout to identify like parts.

BRIEF DESCRIPTION OF THE DRAWINGS

FIGS. I and II each show a possible embodiment of a mammometer of the present invention.

Referring now to FIG. I of the drawing there is illustrated one possible embodiment of the mammometer of this invention. The illustration in FIG. I is drawn to approximately one-half scale. The mammometer 50 is basically a flat or planar substrate preferably made of a clear or transparent material such as glass or a plastic, and while the mammometer shown in FIG. I is circular in shape, it can also be square, rectangular, triangular, eliptical or some other configuration so long as sufficient and proper area is provided for the various measuring means which are described, infra. While not shown in FIG. I, it is contemplated that the article of this invention may be equipped with handles or other means to facilitate holding the device. In addition to or in lieu of such holding means, means may be provided for placing and holding the device in some sort of frame.

Figure 1:
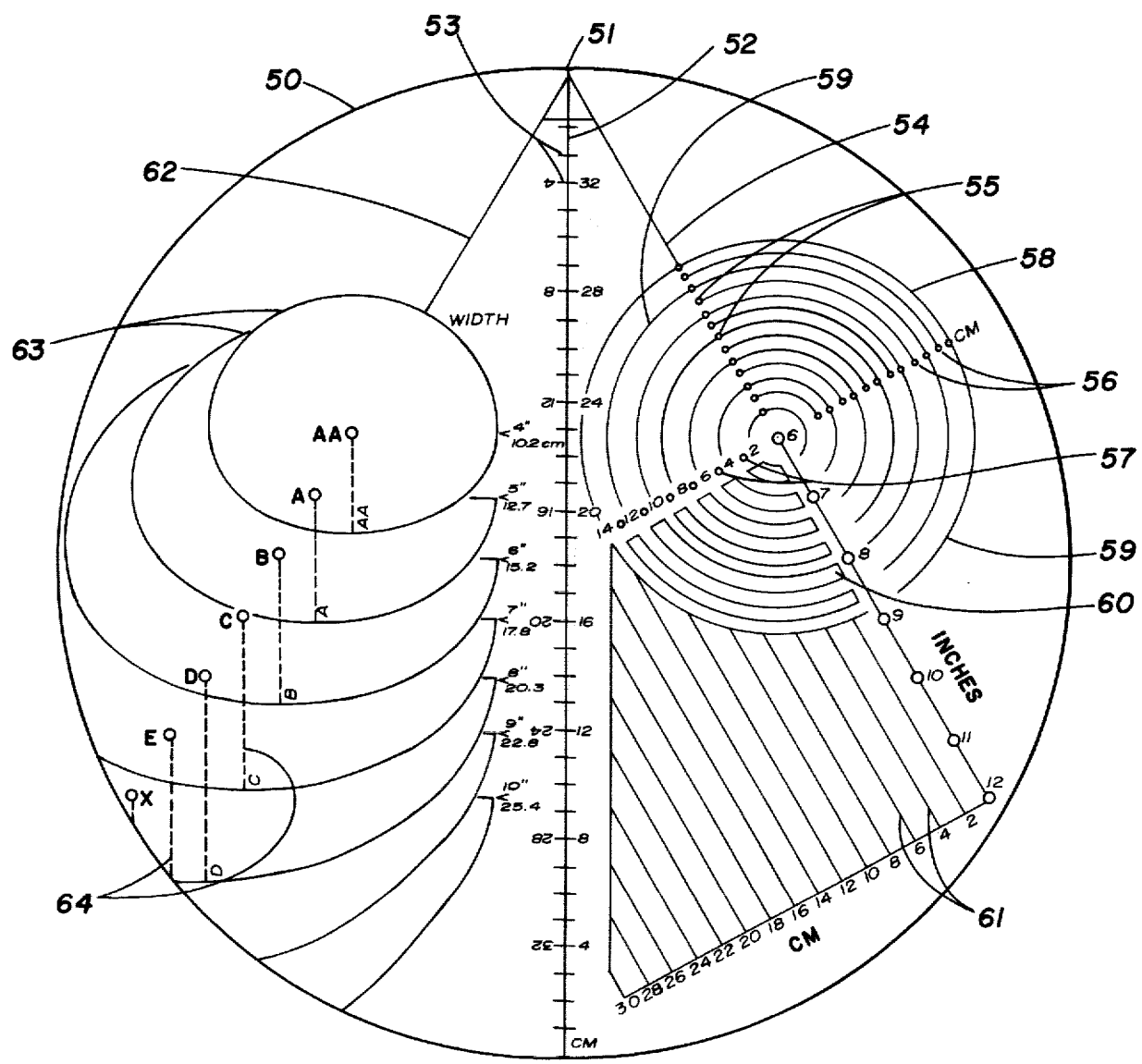
Figure 2:
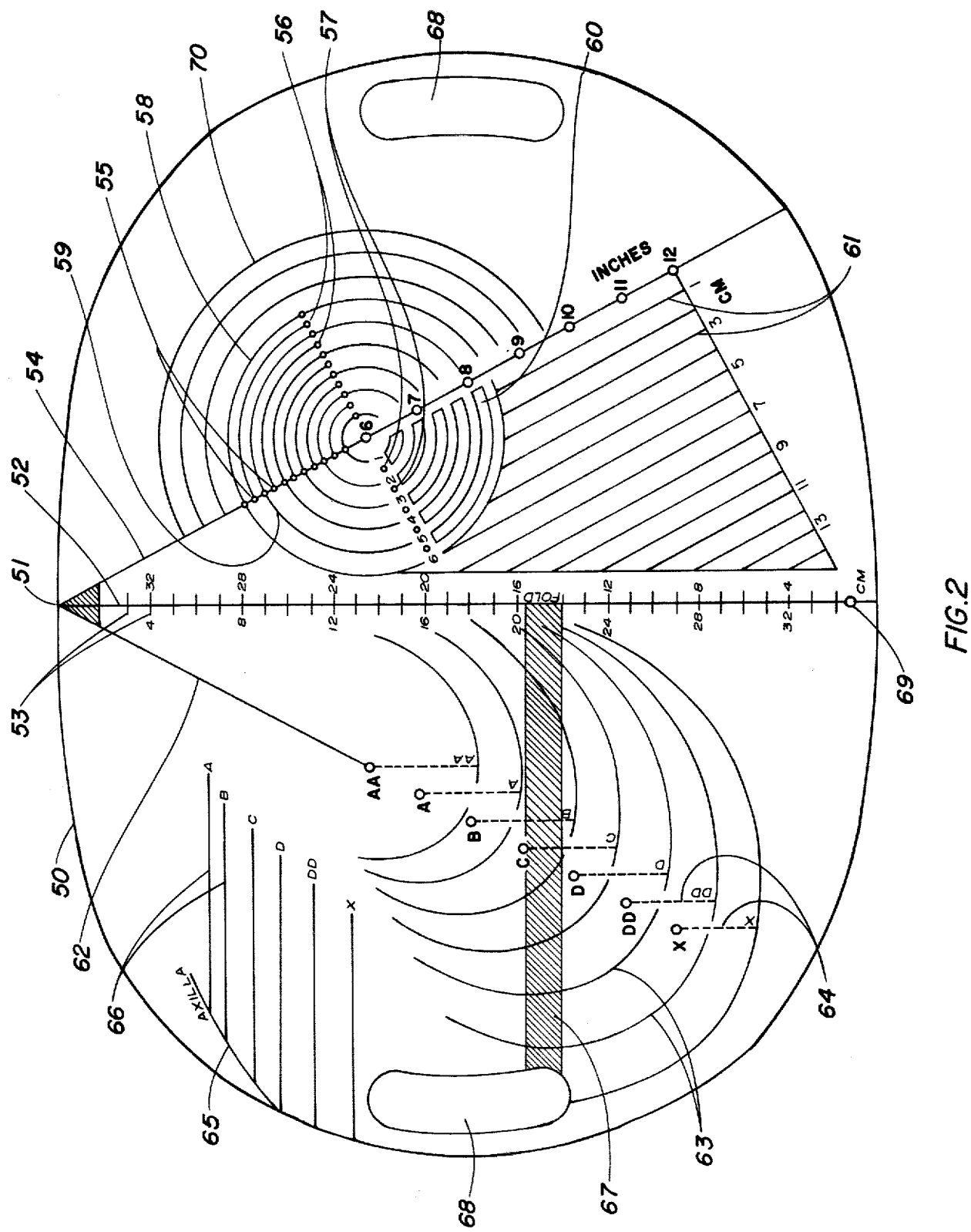

The measuring means can best be defined from and include an equilateral triangle (not fully shown) which is defined in FIG. I by vertex angle 51, aperture X and aperture 12.

The equilateral triangle, if drawn to full scale, would be twelve (12) inches long on each side. It is noted that the sides of the equilateral triangle are not fully drawn in FIG. I, and that FIG. I is representative of how and to what extent the various measuring means will be scribed upon the article made in accordance with this invention.

Various references will be made herein with respect to measuring means being "scribed" upon the substrate. By the term "scribed" it is meant that the measuring means is scratched, grooved, etched, silkscreened, printed, painted, molded, or similarly fixed upon the substrate in the manner and relationships indicated to facilitate the measurements to be made.

There is a linear line or mark 52 scribed upon the substrate which runs from the vertex angle 51 of the equilateral triangle in a direction perpendicular to the base (not shown) of the triangle. The linear mark 52 which is shown in the drawing extends or passes through the base of the triangle to the edge of the mammometer and would be about thirty-six (36) centimeters long if drawn to full scale. It is not essential that this linear mark 52 extend to or pass through the base of the triangle, but it is preferable.

Also upon the substrate there is a series of short linear marks 53 which are scribed perpendicular to linear mark 52. Linear marks 53 extend about equal distance (for appearances sake) on either side of linear mark 52 and would be spaced one (1) centimeter apart if FIG. I were full scale.

It is perhaps worth noting at this point that while measuring units of inches and centimeters are employed in describing the article of this invention, and in the Figures illustrating this invention, it should be obvious to those skilled in the art that other units of measure can be employed. It is believed, however, that the units chosen for purposes of illustration are those which the medical profession would prefer to use.

In use, by placing vertex angle 51 at the sternal notch of the patient with linear mark 52 running from that point towards the umbilicus, that is, with linear mark 52 coinciding with the sternal line, it is possible to make measurements, particularly with regard to symmetry, of the mammary glands with respect to these reference points.

Along the right side 54 of the equilateral triangle a series of apertures are placed which enable the doctor to measure the distance from the sternal notch and/or the umbilicus to the nipple of the breast, depending upon whether the vertex angle 51 is placed at the sternal notch or umbilicus when making the measurement. In FIG. I a series of seven such apertures are shown for purposes of illustration being numbered 6, 7, 8, 9, 10, 11, and 12 respectively. If FIG. I were full scale, these apertures would begin with number 6 located at the midpoint of right side 54 at a distance of six inches from vertex angle 51 and be spaced one inch apart with aperture 12 being the last of the series located at the right base angle of the equilateral triangle.

Also along the right side 54 of the equilateral triangle is another series of apertures 55 which are shown in FIG. I to be located between vertex angle 51 and aperture 6. For purposes of illustration thirteen such apertures are shown which are smaller in size than apertures 6 thru 12. This is advantageous in distinguishing between the two sets of apertures along side 54, but one could make all the apertures of the same of different size if so desired. Likewise, while the apertures in FIG. I are shown to be round or circular, a preferred embodiment from a manufacturing consideration, the apertures can be made in other configurations or shapes. Furthermore, it should be obvious that the numbers of the various apertures illustrated in FIG. I. can be increased or decreased to meet individual preferences or needs. In FIG. I, on a full scale basis, the first aperture 55 is located one centimeter from the midpoint of right side 54 and then are placed or located at one-half centimeter intervals towards vertex angle 51.

The mammometer 50 also contains a series of apertures 56 lying in a line to the right of and perpendicular to the midpoint of right side 54 of the equilateral triangle. Twelve of these apertures are illustrated in FIG. I, the first of which on a a full scale basis is located one and one-half centimeters from the midpoint of right side 54, the remainder of apertures 56 being placed at one-half centimeter intervals.

The mammometer 50 further contains a series of apertures 57 lying in a line to the left of and perpendicular to the midpoint of right side 54 of the equilateral triangle. Six of these apertures are illustrated in FIG. I the first of which on a full scale basis is located one and one-half centimeters from the midpoint of right side 54, the remainder of apertures 57 being placed at one centimeter intervals.

Employing the midpoint of the right side 54 of the equilateral triangle as the center, a series of arcs 58 are scribed between apertures 55 and apertures 56. On an alternating basis, in FIG. I, extensions 59 of these arcs are scribed into quadrants to the left and right of the quadrant defined by the lines of apertures 55 and 56.

In the quadrant opposite the quadrant defined by the lines of apertures 55 and 56, mammometer 50 contains a series of apertures 60 in the shape of trapazoidal arcs. Six such apertures 60 are illustrated in FIG. I, and on a full scale basis apertures 60 would be one-half centimeter in width and spaced one-half centimeter apart. It can be seen from FIG. I that in the preferred embodiment of the invention apertures 60 increase in length as one moves along a line (not shown ) from the midpoint of right side 54 of the equilateral triangle running perpendicularly and outwardly through the midpoints of the trapazoidal arcs.

In FIG. I there is illustrated a series of lines 61 which are parallel to right side 54 of the equilateral triangle, said lines 61 being one centimeter apart on a full scale basis. It is noted that if parallel lines 61 were extended they would intersect with the numbers placed at the points between apertures 57.

In one illustrative use the mammometer 50 is placed over the breast with aperture 6 centered over the nipple. Then with the aid of apertures 55, 56, and/or 57; and with the aid of arcs 58 and/or 59; and with the use of the numbers between apertures 57; and with the use of parallel lines 61; one can measure not only the size of the existing breast, but also can make measurements useful in selecting internal or external prosthetic mammary devices. It is noted that in the article illustrated in FIG. I that the numbers (scale) between apertures 57 and the scale for parallel lines 61 are twice the actual measurement made thus giving the doctor an instant reading of the diameter of the breast. Obviously, the true measurement scale as illustrated in FIG. II (or some other scale) could be used if so desired.

The apertures 55, 56, 57 and 60 also provide the doctor or surgeon with ready means for accurately placing reference marks and lines on the patient's breast. These marks and lines are useful, for example, in various aspects of surgical procedures such as where to make the incisions, the size of the incisions, and how large a surgical pocket to create for the prosthetic device in the case of implants.

Along side 62 of the equilateral triangle a series of apertures are placed. In FIG. I seven such apertures are shown which are labeled AA, A, B, C, D, E, and X. Of these apertures, AA is located at the midpoint of left side 62 and aperture X is located at the left base angle of the equilateral triangle. If FIG. I were full scale, aperture AA would be six inches from vertex angle 51 and each succeeding aperture would be one inch apart. This series of apertures is labeled alphabetically AA thru E in the manner indicated to conform to standard brassiere cup sizes for reasons which will be more fully explained later. Aperture X while not conforming to a standard brassiere cup size is provided as an additional reference point which would be useful, for example, to a surgeon in a reduction mammoplasty operation.

Using apertures AA, A, B, C, D, E, and X as focal points, there is scribed upon mammometer 50 a series of eliptical-like marks 63 which in use define the parameters of a typical mammary gland or breast which corresponds to the aperture scale serving as the focal point. In FIG. I, just to the right of the eliptical-like marks 63 is a width scale which sets forth in inches and centimeters the typical average width of a mammary gland of each size heretofore noted as measured by a line (only partially shown) running parallel to the base of the equilateral triangle and through the apertures AA thru X along the left side 62 of the triangle. This particular scale, while optional, illustrates the fact that a multiscale system can be used if one so desires.

Mammometer 50 also has a series of lines or marks 64 which run in a direction perpendicular to the base of the equilateral triangle. Lines or marks 64 begin at the apertures AA thru X and, so far as physically possible, terminate at the corresponding eliptical-like mark 63. In FIG. I, these lines 64 are dotted in nature and have the corresponding aperture letter(s) placed beside them. These lines 64 are an indication of the typical perpendicular distance from the center of the nipple of the breast to the lowest point of the breast.

During use of mammometer 50, apertures AA thru X, eliptical-like marks 63 and lines 64 are employed by the doctor, surgeon or foundation garment fitter not only to make the appropriate measurements of the existing breasts but also in the selection of the appropriate internal or external prosthetic devices where that is indicated, and in making the necessary measurements relevant to breast surgery, or matching for fitting of an external breast prosthesis.

FIG. II illustrates the most preferred embodiment of the invention at the present time. The numbers and letters in FIG. II which also appeared in FIG. I identify identical or similar parts. The illustration in FIG. II is drawn to approximately one-half scale.

In FIG. II there is illustrated a mammometer 50 consisting of a flat or planar substrate made of a clear or transparent material such as glass or plastic and which is oval or eliptical in shape. The mammometer shown in FIG. II has two apertures 68 which function as handles which facilitate holding and manipulation of the device while it is being used.

The measuring means containing by mammometer 50 illustrated in FIG. II can best be defined with reference to an isosceles triangle (not fully shown) which is defined by vertex angle 51 and base angles at apertures 12 and X.

In FIG. II there is a linear line or mark 52 scribed upon the substrate which runs from the vertex angle 51 of the isosceles triangle in a direction perpendicular to the base (not shown) of the triangle. The linear mark 52 which is shown in the drawing extends or passes through the base of the triangle to the edge of the mammometer and would be about thirty-six (36) centimeters long if drawn to full scale. It is not essential that this linear mark 52 extend to or pass through the base of the triangle, but it is preferable.

Also in FIG. II upon the substrate there is a series of short linear marks 53 which are scribed perpendicular to linear mark 52. Linear marks 53 extend about equal distance (for appearances sake) on either side of linear mark 52 and would be spaced one (1) centimeter apart if the drawing were full scale.

Along the right side 54 of the isosceles triangle in FIG. II a series of apertures are placed which enable the doctor to measure the distance from the sternal notch and/or umbilicus to the nipple of the breast, depending upon whether the vertex angle 51 is placed at the sternal notch or umbilicus when making the measurement. In FIG. II a series of seven such apertures are shown for purposes of illustration being numbered 6, 7, 8, 9, 10, 11, and 12, respectively. If FIG. II were full scale, those apertures would begin with number 6 located at the midpoint of right side 54 at a distance of six inches from vertex angle 51 and be spaced one inch apart with aperture 12 being the last of the series located at the right base angle of the equilateral triangle.

Also along the right side 54 of the isosceles triangle is another series of apertures 55 which are shown in FIG. II to be located between vertex angle 51 and aperture 6. For purposes of illustration eleven such apertures are shown which are smaller in size than apertures 6 thru 12. This is advantageous in distinguishing between the two sets of apertures along side 54, but one could make all the apertures of the same or different size if so desired. In FIG. II, on a full scale basis, the first aperture 55 is located one centimeter from the midpoint of right side 54 and then are placed or located at one-half centimeter intervals towards vertex angle 51.

The mammometer 50 also contains a series of apertures 56 lying in a line to the right of and perpendicular to the midpoint of right side 54 of the isosceles triangle. Eleven of these apertures are illustrated in FIG. II, the first of which on a full scale basis is located one centimeter from the midpoint of right side 54, the remainder of apertures 56 being placed at one-half centimeter intervals.

The mammometer 50 further contains a series of apertures 57 lying in a line to the left of and perpendicular to the midpoint of right side 54 of the isosceles triangle. Five of these apertures are illustrated in FIG. II, the first of which on a full scale basis is located one and one-half centimeters from the midpoint of right side 54, the remainder of apertures 57 being placed at one centimeter intervals.

Employing the midpoint of the right side 54 of the isosceles triangle as the center, a series of arcs 58 are scribed between apertures 55 and apertures 56. On a alternating basis, in FIG. II, extensions 59 of these arcs are scribed into quadrants to the left and right of the quadrant defined by the lines of apertures 55 and 56.

FIG. II also illutrates three arcs 70 scribed upon the mammometer 50 using the midpoint of side 54 (e.g. aperture 6) as the center of the arc and side 54 as the diameter of the circle.

In the quadrant opposite the quadrant defined by the lines of apertures 55 and 56, mammometer 50 contains a series of apertures 60 in the shape of trapazoidal arcs. Five such apertures 60 are illustrated in FIG. II, and on a full scale basis apertures 60 would be one-half centimeter in width and spaced one-half centimeter apart. It can be seen from the drawing that in the preferred embodiment of the invention apertures 60 increase in length as one moves along a line (not shown) from the midpoint of right side 54 of th isosceles triangle running perpendicularly and outwardly through the midpoints of the trapazoidal arcs.

In FIG. II there is illustrated a series of lines 61 which are parallel to right side 54 of the isosceles triangle, said lines 61 being one centimeter apart on a full scale basis.

Along side 62 of the isosceles triangle a series of apertures are placed. In FIG. II seven Such apertures are shown which are labeled AA, A, B, C, D, DD, and X. Of these apertures, AA is located at the midpoint of left side 62 and aperture X is located at the left base angle of the isosceles triangle. If the drawing were full scale, aperture AA would be six inches from vertex angle 51 and each succeeding aperture would be one inch apart. This series of apertures is labeled alphabetically AA thru DD in the manner indicated to conform to standard brassiere cup sizes. The DD designation is now being used by many brassiere manufactures in place of the E designation formerly used. Aperture X while not conforming to a standard brassiere cup size is provided as an additional reference for the doctor's use in cases involving exceptionally large breasts.

In FIG. II, using apertures AA, A, B, C, D, DD, and X as focal points, there is scribed upon mammometer 50 a series of eliptical-like marks 63 which in use define the parameters of a typical mammary gland or breast which corresponds to the aperture scale serving as the focal point.

Mammometer 50 also has a series of lines or marks 64 which run in a direction perpendicular to the base of the isosceles triangle. Lines or marks 64 begin at the apertures AA thru X and terminate at the corresponding eliptical-like mark 63. In FIG. II, these lines 64 are dotted in nature and have the corresponding aperture letter(s) placed beside them. These lines 64 are an indication of the typical perpendicular distance from the center of the nipple of the breast to the lowest point of the breast.

The mammometer 50 illustrated in FIG. II has scribed on the left side thereof a curved line 65 which line is also labeled "axilla." Extending to the right from line 65 is a series of parallel lines labeled A, B, C, D, DD, and X. In use, for example, the point of intersection of line 65 and line 66A is placed at the patients axilla and aperture A is placed over the nipple of the breast, then line 66A would define the top of the breast tissue for a typical breast of that size. It should be noted at this point that while at first glance it would appear that the article of this invention provides a means for making measurement with respect to only one of the breasts, when made of a clear or transparent materials as is preferred, the doctor need merely flip the mammometer over for making the measurements of the other breast.

In the mammometer illustrated in FIG. II there is a shaded band 67 with the word "fold" at the right end. This shaded band or area 67 is defined by a pair of lines parallel to the base of the triangle and lies between apertures C and D. This shaded band 67 defines the typical location of the inframammary fold for all breasts relating to a brassiere size of C or larger.

Finally, in the mammometer in FIG. II there is provided an aperture 69 on line 52 through which aperture 69 a rod (not shown) can be inserted. On the patient side of the mammometer there is perpendicularly attached to said rod another rod or disk (not shown). When the resulting "T" shaped combination of rods or the "umbrella" shaped combination of rod and disk are used with the mammometer they serve as a means for steadying the article against the patient and keeping it in a proper plane with regard to the patient.

The examples of how the mammometer illustrated in FIG. I can be used to make measurements of the breast are equally applicable to the mammometer of FIG. II and are not repeated here for the sake of brevity.

While FIGS. I and II and above description show two possible embodiments of the present invention and teaches those skilled in the art how it can be used, other modifications, variations and uses of the invention will now be obvious to those skilled in the art and are within the scope of the appended claims.

That which is claimed is:

1. An article of manufacture useful for making measurements of and relative to mammary glands, said article comprising a planar substrate of a transparent material, said planar substrate containing
   (A) means for measuring distances along a line running from the sternal notch to the umbilicus;
   (B) means for measuring the distance from the sternal notch and/or the umbilicus to the nipple;
   (C) means for measuring the size of mammary glands relative to standard brassiere cup sizes;
   (D) means for measuring the perpendicular distance from the nipple to the lowest point of a mammary gland, relative to mammary glands of typical sizes;
   (E) means for measuring distances concentrically from the nipple, which means is also useful for measuring and selecting the appropriate size mammary prosthesis; and
   (F) means for locating and assisting in placing guideline marks preparatory to surgery on a mammary gland.

2. An article as defined in claim 1 wherein
   (A) consists essentially of a series of linear marks,
   (B) consists essentially of a linear series of apertures,
   (C) consists essentially of another linear series of apertures, each of these apertures serving as the center for an eliptical-like mark,
   (D) consists essentially of a series of parallel linear marks originating at apertures (C),
   (E) consists essentially of a series of concentric marks, and
   (F) consists essentially of two linear series of apertures which series are perpendicular to one another, and a series of apertures in the shape of trapazoidal arcs, and all marks referred to hereinabove being scribed upon the planar substrate.

3. An article of manufacture useful for making measurements of and relative to mammary glands, said article comprising a planar substrate of a transparent material, there being located on said substrate various measuring means, said measuring means being placed on said substrate with reference to the sides of an equilateral triangle whose sides are each twelve (12) inches in length, said measuring means including:
   (A) a linear mark scribed from the vertex angle of the equilateral triangle, perpendicular to the base of the triangle, and passing through the base of the triangle, this linear mark being about thirty-six (36) centimeters long;
   (B) short linear marks scribed perpendicular to mark (A) and which extend approximately equal distance on either side of (A), these short linear marks being spaced one (1) centimeter apart beginning from the vertex angle of the equilateral triangle;
   (C) along the right and left sides of the equilateral triangle, beginning at the midpoint of these sides and terminating at the base angles of the triangle, there being a series of about seven (7) apertures spaced one (1) inch apart;
   (D) with the apertures (C) along the left side of the equilateral triangle serving as the focal points at the center of the nipple of the mammary gland, and beginning with the aperture at the midpoint of the left side of the triangle serving as the focal point for an AA size mammary gland and then proceeding towards the base angle allowing the succeeding apertures serve as the focal points of A, B, C, D, E, and X size mammary glands respectively, there being eliptical-like marks scribed around said focal points which define the parameters of typical mammary glands of the aforementioned sizes;
   (E) there being scribed to one side of the eliptical-like marks (D) the width of a typical mammary gland of each size heretofore noted as measured by lines running parallel to the base of the equilateral triangle and through the center of apertures (C) along the left side of the triangle, and terminating on each end where the lines intersect eliptical-like marks (D);
   (F) there being scribed lines from the apertures (C) along the left side of the equilateral triangle to the bottom of the corresponding eliptical-like marks (D), these lines running in a direction perpendicular to the base of the triangle and being a measure of the distance from the center of the nipple to the lowest point of the mammary gland for typical mammary glands of the heretofore indicated sizes;
   (G) along the right side of the equilateral triangle there being a series of about thirteen (13) apertures beginning one (1) centimeter from the midpoint of the side and running towards the vertex angle at intervals of one-half ($\frac{1}{2}$) centimeter;
   (H) there being a series of about twelve (12) apertures in a line to the right of and perpendicular to the midpoint of the right side of the equilateral triangle, these apertures beginning one and one-half (1$\frac{1}{2}$) centimeters from the midpoint of the right side and being spaced one-half ($\frac{1}{2}$) centimeter apart;
   (I) there being a series of about six (6) apertures in a line to the left of and perpendicular to the midpoint of the right side of the equilateral triangle, these apertures beginning one and one-half (1$\frac{1}{2}$) centimeters from the midpoint of the right side and being spaced one (1) centimeter apart;
   (J) employing the midpoint of the right side of the equilateral triangle as the center of a series of concentric circles, arcs are scribed between each aperture of (G) and (H), alternate arcs being extended into the quadrants to the left and right of the quadrant defined by apertures (G) and (H);
   (K) in the quadrant opposite to the quadrant defined by apertures (G) and (H) there being a series of about six (6) apertures in the shape of trapazoidal arcs which are one-half ($\frac{1}{2}$) centimeter apart, said apertures all being one-half ($\frac{1}{2}$) centimeter in width but of increasing length as one moves along a line from the midpoint of the right side of the equilateral triangle running perpendicularly and outwardly through the midpoints of the trapazoidal arcs; and (L) there being a series of lines one (1) centimeter apart scribed parallel to the right side of the equilateral triangle.

4. An article as defined in claim 1 wherein
(A) consists essentially of a series of linear marks,
(B) consists essentially of a linear series of apertures,
(C) consists essentially of another linear series of apertures, each of these apertures serving as the center for an eliptical-like mark,
(D) consists essentially of a series of parallel linear marks originating at apertures (C),
(E) consists essentially of a series of concentric marks, and
(F) consists essentially of two linear series of apertures which series are perpendicular to one another, and a series of apertures in the shape of trapazoidal arcs, and all marks referred to hereinabove being silk-screened upon the planar substrates.

5. An article of manufacture useful for making measurements of and relative to mammary glands, said article comprising a planar substrate of a transparent material, there being located on said substrate various measuring means, said measuring means being placed on said substrate with reference to the sides of an isosceles triangle whose sides are each about twelve (12) inches in length, said measuring means including:
(A) a linear mark scribed from the vertex angle of the isosceles triangle, perpendicular to the base of the triangle, and passing through the base of the triangle, this linear mark being about thirty-six (36) centimeters long;
(B) short linear marks scribed perpendicular to mark (A) and which extend approximately equal distance on either side of (A), these short linear marks being spaced one (1) centimeter apart beginning from the vertex angle of the isosceles triangle;
(C) along the right and left sides of the isosceles triangle, beginning at the midpoint of these sides and terminating at the base angles of the triangle, there being a series of about seven (7) apertures spaced one (1) inch apart;
(D) with the apertures (C) along the left side of the isosceles triangle serving as the focal points at the center of the nipple of the mammary gland, and beginning with the aperture at the midpoint of the left side of the triangle serving as the focal point for an AA size mammary gland and then proceeding towards the base angle allowing the succeeding apertures serve as the focal points A, B, C, D, DD and X size mammary glands respectively, there being eliptical-like marks scribed around said focal points which define the parameters of typical mammary glands of the aforementioned sizes;
(E) there being scribed lines from the apertures (C) along the left side of the isosceles triangle to the bottom of the corresponding eliptical-like marks (D), these lines running in a direction perpendicular to the base of the triangle and being a measure of the distance from the center of the nipple to the lowest point of the mammary gland for typical mammary glands of the heretofore indicated sizes;
(F) along the right side of the isosceles triangle there being a series of about eleven (11) apertures beginning one (1) centimeter from the midpoint of the side and running towards the vertex angle at intervals of one-half (½) centimeter;
(G) there being a series of about eleven (11) apertures in a line to the right of and perpendicular to the midpoint of the right side of the isosceles triangle, these apertures beginning one centimeter from the midpoint of the right side and being spaced one-half (½) centimeter apart;
(H) there being a series of about five (5) apertures in a line to the left of and perpendicular to the midpoint of the right side of the isosceles triangle, these apertures beginning one and one-half (1½) centimeters from the midpoint of the right side and being spaced one (1) centimeter apart;
(I) employing the midpoint of the right side of the isosceles triangle as the center of a series of concentric circles, arcs are scribed between each aperture of (F) and (G), alternate arcs being extended into the quadrants to the left and right of the quadrant defined by apertures (F) and (G);
(J) in the quadrant opposite to the quadrant defined by apertures (F) and (G) there being a series of about five (5) apertures in the shape of trapazoidal arcs which are one-half (½) centimeter apart, said apertures all being one-half (½) centimeter in width but of increasing length as one moves along a line from the midpoint of the right side of the isosceles triangle running perpendicularly and outwardly through the midpoints of the trapazoidal arcs;
(K) there being a series of lines one (1) centimeter apart scribed parallel to the right side of the isosceles triangle;
(L) there being a curved line outside and to the left of the isosceles triangle having a series of parallel lines extending therefrom, said parallel lines also being parallel to the base of the triangle, said curved line and parallel lines being situated so that when their intersection is placed at the axilla they cooperate with apertures (C) in locating the top of the mammary gland tissue;
(M) there being a shaded band defined by a pair of lines lying between the forth and fifth apertures (C) counting from the vertex angle, said pair of lines being parallel to the base of the triangle and perpendicular to and terminating at linear mark (A); and
(N) means for holding the article.

* * * * *